(12) United States Patent  
Jelich et al.

(10) Patent No.: US 8,518,060 B2
(45) Date of Patent: Aug. 27, 2013

(54) MEDICAL CLIP WITH RADIAL TINES, SYSTEM AND METHOD OF USING SAME

(75) Inventors: Damian Jelich, Cottage Grove, MN (US); Morgan House, Newfields, NH (US); Nareak Douk, Lowell, MA (US); Rany Huynh, Charlestown, MA (US)

(73) Assignee: Medtronic, Inc., Minneapolis, MN (US)

( * ) Notice: Subject to any disclaimer, the term of this patent is extended or adjusted under 35 U.S.C. 154(b) by 522 days.

(21) Appl. No.: 12/421,360

(22) Filed: Apr. 9, 2009

(65) Prior Publication Data

US 2010/0262167 A1 Oct. 14, 2010

(51) Int. Cl.
*A61B 17/122* (2006.01)

(52) U.S. Cl.
USPC .......................................... 606/151; 606/213

(58) Field of Classification Search
USPC ......... 606/142, 143, 151, 157, 158, 213–217, 606/219, 221, 139, 220; 24/3.11, 391, 394, 24/509, 510, 548–550
See application file for complete search history.

(56) References Cited

U.S. PATENT DOCUMENTS

| | | |
|---|---|---|
| 43,098 A | 6/1864 | Cooper |
| 636,728 A | 11/1899 | Kindel |
| 655,190 A | 8/1900 | Bramson |
| 1,087,186 A | 2/1914 | Scholfield |
| 1,167,014 A | 1/1916 | O'Brien |
| 1,539,221 A | 5/1925 | Tennant |
| 1,583,271 A | 5/1926 | Biro |
| 1,625,602 A | 4/1927 | Gould et al. |
| 1,867,624 A | 7/1932 | Hoffman |
| 2,201,610 A | 5/1940 | Dawson, Jr. |
| 2,240,330 A | 4/1941 | Flagg et al. |
| 2,256,382 A | 9/1941 | Dole |
| 2,264,679 A | 12/1941 | Ravel |
| 2,413,142 A | 12/1946 | Jones et al. |
| 2,430,293 A | 11/1947 | Howells |
| 2,505,358 A | 4/1950 | Gusberg et al. |
| 2,516,710 A | 7/1950 | Mascolo |
| 2,715,486 A | 8/1955 | Marcoff-Moghadam et al. |
| 2,890,519 A | 6/1959 | Storz, Jr. |
| 2,940,452 A | 6/1960 | Smialowski |
| 3,055,689 A | 9/1962 | Jorgensen |
| 3,057,355 A | 10/1962 | Smialowski et al. |
| 3,082,426 A | 3/1963 | Miles |
| 3,143,742 A | 8/1964 | Cromie |
| 3,150,379 A | 9/1964 | Brown |
| 3,180,337 A | 4/1965 | Smialowksi |
| 3,249,104 A | 5/1966 | Hohnstein |
| 3,274,658 A | 9/1966 | Pile |

(Continued)

FOREIGN PATENT DOCUMENTS

| DE | 219999 | 3/1910 |
|---|---|---|
| DE | 377052 | 6/1923 |

(Continued)

OTHER PUBLICATIONS

US 6,503,260, 01/2003, Schaller et al. (withdrawn)

*Primary Examiner* — Kathleen Holwerda

(57) ABSTRACT

Device, system and method for drawing together patient tissue. A central hub has an axis. Several tines are coupled to the central hub. Each of the tines has a tip and is resiliently biased to form a coil. Each tip points radially outward from the axis, with an approximately common angle between adjacent ones of the tines.

19 Claims, 6 Drawing Sheets

(56) References Cited

U.S. PATENT DOCUMENTS

| | | |
|---|---|---|
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,776,237 A | 12/1973 | Hill et al. |
| 3,786,816 A | 1/1974 | Wolvek |
| 3,802,438 A | 4/1974 | Wolvek |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A | 9/1975 | Smith et al. |
| 3,908,662 A | 9/1975 | Razgulov et al. |
| 3,910,281 A | 10/1975 | Kletschka et al. |
| 3,958,576 A | 5/1976 | Komiya |
| 3,976,079 A | 8/1976 | Samuels et al. |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A | 7/1980 | Sakura, Jr. |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Klieman et al. |
| 4,523,592 A | 6/1985 | Daniel |
| 4,532,927 A | 8/1985 | Miksza, Jr. |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen, II et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon et al. |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,178,634 A | 1/1993 | Ramos Martinez |
| 5,192,294 A | 3/1993 | Blake, III |
| 5,196,022 A | 3/1993 | Bilweis |
| 5,201,880 A | 4/1993 | Wright et al. |
| 5,207,694 A | 5/1993 | Broome |
| 5,217,027 A | 6/1993 | Hermens |
| 5,219,358 A | 6/1993 | Bendel et al. |
| 5,221,259 A | 6/1993 | Weldon et al. |
| 5,222,961 A | 6/1993 | Nakao et al. |
| 5,222,976 A | 6/1993 | Yoon |
| 5,234,447 A | 8/1993 | Kaster et al. |
| 5,236,440 A | 8/1993 | Hlavacek |
| 5,242,456 A | 9/1993 | Nash et al. |
| 5,242,457 A | 9/1993 | Akopov et al. |
| 5,246,443 A | 9/1993 | Mai |
| 5,250,053 A | 10/1993 | Snyder |
| 5,258,011 A | 11/1993 | Drews |
| 5,261,917 A | 11/1993 | Hasson et al. |
| 5,269,783 A | 12/1993 | Sander |
| 5,269,809 A | 12/1993 | Hayhurst et al. |
| 5,282,825 A | 2/1994 | Muck et al. |
| 5,290,289 A | 3/1994 | Sanders et al. |
| 5,304,117 A | 4/1994 | Wilk |
| 5,304,204 A | 4/1994 | Bregen |
| 5,306,296 A | 4/1994 | Wright et al. |
| 5,312,436 A | 5/1994 | Coffey et al. |

| Patent | Date | Inventor |
|---|---|---|
| 5,314,468 A | 5/1994 | Ramos Martinez |
| 5,330,503 A | 7/1994 | Yoon |
| 5,334,196 A | 8/1994 | Scott et al. |
| 5,336,233 A | 8/1994 | Chen |
| 5,336,239 A | 8/1994 | Gimpelson |
| 5,346,459 A | 9/1994 | Allen |
| 5,350,420 A | 9/1994 | Cosgrove et al. |
| 5,353,804 A | 10/1994 | Kornberg et al. |
| 5,355,897 A | 10/1994 | Pietrafitta et al. |
| 5,356,424 A | 10/1994 | Buzerak et al. |
| 5,364,406 A | 11/1994 | Sewell, Jr. |
| 5,366,459 A | 11/1994 | Yoon |
| 5,366,462 A | 11/1994 | Kaster et al. |
| 5,366,479 A | 11/1994 | McGarry et al. |
| 5,374,268 A | 12/1994 | Sander |
| 5,376,096 A | 12/1994 | Foster |
| 5,382,259 A | 1/1995 | Phelps et al. |
| 5,383,904 A | 1/1995 | Totakura et al. |
| 5,387,227 A | 2/1995 | Grice |
| 5,403,331 A | 4/1995 | Chesterfield et al. |
| 5,403,333 A | 4/1995 | Kaster et al. |
| 5,403,338 A | 4/1995 | Milo |
| 5,403,346 A | 4/1995 | Loeser |
| 5,413,584 A | 5/1995 | Schulze |
| 5,417,684 A | 5/1995 | Jackson et al. |
| 5,417,700 A | 5/1995 | Egan |
| 5,423,821 A | 6/1995 | Pasque |
| 5,431,666 A | 7/1995 | Sauer et al. |
| 5,437,680 A | 8/1995 | Yoon |
| 5,437,681 A | 8/1995 | Meade et al. |
| 5,437,685 A | 8/1995 | Blasnik |
| 5,439,479 A | 8/1995 | Shichman et al. |
| 5,445,167 A | 8/1995 | Yoon et al. |
| 5,445,644 A | 8/1995 | Pietrafitta et al. |
| 5,450,860 A | 9/1995 | O'Connor |
| 5,451,231 A | 9/1995 | Rabenau et al. |
| 5,452,733 A | 9/1995 | Sterman et al. |
| 5,454,834 A | 10/1995 | Boebel et al. |
| 5,456,246 A | 10/1995 | Schmieding et al. |
| 5,462,561 A | 10/1995 | Voda |
| 5,474,557 A | 12/1995 | Mai |
| 5,480,405 A | 1/1996 | Yoon |
| 5,486,187 A | 1/1996 | Schenck |
| 5,486,197 A | 1/1996 | Le et al. |
| 5,488,958 A | 2/1996 | Topel et al. |
| 5,496,334 A | 3/1996 | Klundt et al. |
| 5,499,990 A | 3/1996 | Schulken et al. |
| 5,500,000 A | 3/1996 | Feagin et al. |
| 5,527,342 A | 6/1996 | Pietrzak et al. |
| 5,533,236 A | 7/1996 | Tseng |
| 5,538,509 A | 7/1996 | Dunlap et al. |
| 5,545,214 A | 8/1996 | Stevens |
| 5,549,619 A | 8/1996 | Peters et al. |
| 5,552,884 A | 9/1996 | Li et al. |
| 5,556,411 A | 9/1996 | Taoda et al. |
| 5,562,685 A | 10/1996 | Mollenauer et al. |
| 5,569,205 A | 10/1996 | Hart et al. |
| 5,569,274 A | 10/1996 | Rapacki et al. |
| 5,569,301 A | 10/1996 | Granger et al. |
| 5,571,119 A | 11/1996 | Atala |
| 5,571,175 A | 11/1996 | Vanney et al. |
| 5,582,616 A | 12/1996 | Bolduc et al. |
| 5,582,619 A | 12/1996 | Ken |
| 5,584,879 A | 12/1996 | Reimold et al. |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup III |
| 5,597,378 A | 1/1997 | Jervis |
| 5,601,571 A | 2/1997 | Moss |
| 5,601,572 A | 2/1997 | Middleman et al. |
| 5,601,600 A | 2/1997 | Ton |
| 5,603,718 A | 2/1997 | Xu |
| 5,609,608 A | 3/1997 | Benett et al. |
| 5,628,757 A | 5/1997 | Hasson |
| 5,630,540 A | 5/1997 | Blewett |
| 5,632,752 A | 5/1997 | Buelna |
| 5,632,753 A | 5/1997 | Loeser |
| 5,643,295 A | 7/1997 | Yoon |
| 5,643,305 A | 7/1997 | Al-Tameem |
| 5,645,568 A | 7/1997 | Chervitz et al. |
| 5,653,716 A | 8/1997 | Malo et al. |
| 5,653,718 A | 8/1997 | Yoon |
| 5,658,312 A | 8/1997 | Green et al. |
| 5,660,186 A | 8/1997 | Bachir |
| 5,665,109 A | 9/1997 | Yoon |
| 5,669,918 A | 9/1997 | Balazs et al. |
| 5,676,670 A | 10/1997 | Kim |
| 5,683,417 A | 11/1997 | Cooper |
| 5,690,662 A | 11/1997 | Chiu et al. |
| 5,695,504 A | 12/1997 | Gifford, III et al. |
| 5,695,505 A | 12/1997 | Yoon |
| 5,697,913 A | 12/1997 | Sierocuk et al. |
| 5,697,943 A | 12/1997 | Sauer et al. |
| 5,700,270 A | 12/1997 | Peyser et al. |
| 5,700,271 A | 12/1997 | Whitfield et al. |
| 5,702,412 A | 12/1997 | Popov et al. |
| 5,707,362 A | 1/1998 | Yoon |
| 5,707,380 A | 1/1998 | Hinchliffe et al. |
| 5,709,693 A | 1/1998 | Taylor |
| 5,709,695 A | 1/1998 | Northrup, III |
| 5,715,987 A | 2/1998 | Kelley et al. |
| 5,720,755 A | 2/1998 | Dakov |
| 5,725,135 A | 3/1998 | Daniel |
| 5,725,539 A | 3/1998 | Matern |
| 5,725,542 A | 3/1998 | Yoon |
| 5,732,872 A | 3/1998 | Bolduc et al. |
| 5,735,290 A | 4/1998 | Sterman et al. |
| 5,746,753 A | 5/1998 | Sullivan et al. |
| 5,755,778 A | 5/1998 | Kleshinski |
| 5,766,189 A | 6/1998 | Matsuno |
| 5,769,870 A | 6/1998 | Salahieh et al. |
| 5,779,718 A | 7/1998 | Green et al. |
| 5,782,397 A | 7/1998 | Koukline |
| 5,782,844 A | 7/1998 | Yoon et al. |
| 5,797,920 A | 8/1998 | Kim |
| 5,797,933 A | 8/1998 | Snow et al. |
| 5,797,934 A | 8/1998 | Rygaard |
| 5,797,960 A | 8/1998 | Stevens et al. |
| 5,799,661 A | 9/1998 | Boyd et al. |
| 5,799,857 A | 9/1998 | Robertson et al. |
| 5,810,848 A | 9/1998 | Hayhurst |
| 5,810,851 A | 9/1998 | Yoon |
| 5,810,853 A | 9/1998 | Yoon |
| 5,810,882 A | 9/1998 | Bolduc et al. |
| 5,817,113 A | 10/1998 | Gifford, III et al. |
| 5,820,631 A | 10/1998 | Nobles |
| 5,824,002 A | 10/1998 | Gentelia et al. |
| 5,824,008 A | 10/1998 | Bolduc et al. |
| 5,827,265 A | 10/1998 | Glinsky et al. |
| 5,827,316 A | 10/1998 | Young et al. |
| 5,830,221 A | 11/1998 | Stein et al. |
| 5,830,222 A | 11/1998 | Makower |
| 5,833,698 A | 11/1998 | Hinchliffe et al. |
| 5,849,019 A | 12/1998 | Yoon |
| 5,851,216 A | 12/1998 | Allen |
| 5,855,614 A | 1/1999 | Stevens et al. |
| 5,868,702 A | 2/1999 | Stevens et al. |
| 5,868,763 A | 2/1999 | Spence et al. |
| 5,871,528 A | 2/1999 | Camps et al. |
| 5,879,371 A | 3/1999 | Gardiner et al. |
| 5,881,943 A | 3/1999 | Heck et al. |
| 5,882,340 A | 3/1999 | Yoon |
| 5,891,130 A | 4/1999 | Palermo et al. |
| 5,891,160 A | 4/1999 | Williamson, IV et al. |
| 5,893,369 A | 4/1999 | LeMole |
| 5,893,865 A | 4/1999 | Swindle et al. |
| 5,893,886 A | 4/1999 | Zegdi et al. |
| 5,895,394 A | 4/1999 | Kienzle et al. |
| 5,904,697 A | 5/1999 | Gifford, III et al. |
| 5,908,428 A | 6/1999 | Scirica et al. |
| 5,911,352 A | 6/1999 | Racenet et al. |
| 5,919,207 A | 7/1999 | Taheri |
| 5,931,842 A | 8/1999 | Goldsteen et al. |
| 5,941,434 A | 8/1999 | Green |
| 5,941,442 A | 8/1999 | Geiste et al. |
| 5,941,888 A | 8/1999 | Wallace et al. |
| 5,941,908 A | 8/1999 | Goldsteen et al. |

| | | | | | | |
|---|---|---|---|---|---|---|
| 5,944,730 A | 8/1999 | Nobles et al. | 6,280,460 B1 | 8/2001 | Bolduc et al. | |
| 5,951,576 A | 9/1999 | Wakabayashi | 6,283,979 B1 | 9/2001 | Mers Kelly et al. | |
| 5,951,600 A | 9/1999 | Lemelson | 6,296,622 B1 | 10/2001 | Kurz et al. | |
| 5,954,735 A | 9/1999 | Rygaard | 6,296,656 B1 | 10/2001 | Bolduc et al. | |
| 5,957,363 A | 9/1999 | Heck | 6,306,141 B1 | 10/2001 | Jervis | |
| 5,957,938 A | 9/1999 | Zhu et al. | 6,332,893 B1 | 12/2001 | Mortier et al. | |
| 5,957,940 A | 9/1999 | Tanner et al. | 6,346,074 B1 | 2/2002 | Roth | |
| 5,961,481 A | 10/1999 | Sterman et al. | 6,346,112 B2 | 2/2002 | Adams | |
| 5,961,539 A | 10/1999 | Northrup, III et al. | 6,350,269 B1 | 2/2002 | Shipp et al. | |
| 5,964,772 A | 10/1999 | Bolduc et al. | 6,352,543 B1 | 3/2002 | Cole | |
| 5,964,782 A | 10/1999 | Lafontaine et al. | 6,358,258 B1 | 3/2002 | Arcia et al. | |
| 5,972,024 A | 10/1999 | Northrup, III et al. | 6,361,559 B1 | 3/2002 | Houser et al. | |
| 5,976,159 A | 11/1999 | Bolduc et al. | 6,368,348 B1 | 4/2002 | Gabbay | |
| 5,976,161 A | 11/1999 | Kirsch et al. | 6,371,964 B1 | 4/2002 | Vargas et al. | |
| 5,976,164 A | 11/1999 | Bencini et al. | 6,387,105 B1 | 5/2002 | Gifford, III et al. | |
| 5,976,178 A | 11/1999 | Goldsteen et al. | 6,391,038 B1 | 5/2002 | Vargas et al. | |
| 5,984,917 A | 11/1999 | Fleischman et al. | 6,402,764 B1 | 6/2002 | Hendricksen et al. | |
| 5,984,959 A | 11/1999 | Robertson et al. | 6,406,492 B1 | 6/2002 | Lytle | |
| 5,989,242 A | 11/1999 | Saadat et al. | 6,406,493 B1 | 6/2002 | Tu et al. | |
| 5,989,268 A | 11/1999 | Pugsley, Jr. et al. | 6,409,739 B1 | 6/2002 | Nobles et al. | |
| 5,989,276 A | 11/1999 | Houser et al. | 6,409,758 B2 | 6/2002 | Stobie et al. | |
| 5,989,278 A | 11/1999 | Mueller | 6,416,527 B1 | 7/2002 | Berg et al. | |
| 5,993,468 A | 11/1999 | Rygaard | 6,418,597 B1 | 7/2002 | Deschenes et al. | |
| 5,997,556 A | 12/1999 | Tanner | 6,419,658 B1 | 7/2002 | Restelli et al. | |
| 6,001,110 A | 12/1999 | Adams | 6,419,681 B1 | 7/2002 | Vargas et al. | |
| 6,007,544 A | 12/1999 | Kim | 6,419,695 B1 | 7/2002 | Gabbay | |
| 6,010,531 A | 1/2000 | Donlon et al. | 6,425,900 B1 | 7/2002 | Knodel et al. | |
| 6,013,084 A | 1/2000 | Ken et al. | 6,428,550 B1 | 8/2002 | Vargas et al. | |
| 6,022,367 A | 2/2000 | Sherts | 6,428,555 B1 | 8/2002 | Koster, Jr. | |
| 6,024,748 A | 2/2000 | Manzo et al. | 6,451,048 B1 | 9/2002 | Berg et al. | |
| 6,032,849 A | 3/2000 | Mastri et al. | 6,461,320 B1 | 10/2002 | Yencho et al. | |
| 6,033,419 A | 3/2000 | Hamblin, Jr. et al. | 6,475,222 B1 | 11/2002 | Berg et al. | |
| 6,036,699 A | 3/2000 | Andreas et al. | 6,478,804 B2 | 11/2002 | Vargas et al. | |
| 6,036,703 A | 3/2000 | Evans et al. | 6,485,496 B1 | 11/2002 | Suyker et al. | |
| 6,036,710 A | 3/2000 | McGarry et al. | 6,491,707 B2 | 12/2002 | Makower et al. | |
| 6,041,607 A | 3/2000 | Kim | 6,497,671 B2 | 12/2002 | Ferrera et al. | |
| 6,056,751 A | 5/2000 | Fenton, Jr. | 6,497,710 B2 | 12/2002 | Yencho et al. | |
| 6,063,070 A | 5/2000 | Eder | 6,514,265 B2 | 2/2003 | Ho et al. | |
| 6,066,148 A | 5/2000 | Rygaard | 6,517,558 B2 | 2/2003 | Gittings et al. | |
| 6,074,401 A | 6/2000 | Gardiner et al. | 6,524,338 B1 | 2/2003 | Gundry | |
| 6,074,418 A | 6/2000 | Buchanan et al. | 6,533,812 B2 | 3/2003 | Swanson et al. | |
| 6,077,291 A | 6/2000 | Das | 6,537,288 B2 | 3/2003 | Vargas et al. | |
| 6,080,114 A | 6/2000 | Russin | 6,547,799 B2 | 4/2003 | Hess et al. | |
| 6,083,237 A | 7/2000 | Huitema et al. | 6,551,332 B1 | 4/2003 | Nguyen et al. | |
| 6,106,538 A | 8/2000 | Shiber | 6,562,053 B2 | 5/2003 | Schulze | |
| 6,110,188 A | 8/2000 | Narciso, Jr. | 6,575,985 B2 | 6/2003 | Knight et al. | |
| 6,113,611 A * | 9/2000 | Allen et al. ................ 606/151 | 6,589,255 B2 | 7/2003 | Schulze et al. | |
| 6,113,612 A | 9/2000 | Swanson et al. | 6,607,541 B1 | 8/2003 | Gardiner et al. | |
| 6,120,524 A | 9/2000 | Taheri | 6,607,542 B1 | 8/2003 | Wild | |
| 6,132,438 A | 10/2000 | Fleischman et al. | 6,613,059 B2 | 9/2003 | Schaller et al. | |
| 6,139,540 A | 10/2000 | Rost et al. | 6,629,988 B2 | 10/2003 | Weadock | |
| 6,143,004 A | 11/2000 | Davis et al. | 6,635,214 B2 | 10/2003 | Rapacki et al. | |
| 6,149,658 A | 11/2000 | Gardiner et al. | 6,638,297 B1 * | 10/2003 | Huitema ..................... 606/219 | |
| 6,152,935 A | 11/2000 | Kammerer et al. | 6,641,593 B1 | 11/2003 | Schaller et al. | |
| 6,152,937 A | 11/2000 | Peterson et al. | 6,648,900 B2 | 11/2003 | Fleischman et al. | |
| 6,159,165 A | 12/2000 | Ferrera et al. | 6,651,670 B2 | 11/2003 | Rapacki et al. | |
| 6,159,225 A | 12/2000 | Makower | 6,651,672 B2 | 11/2003 | Roth | |
| 6,165,183 A | 12/2000 | Kuehn et al. | 6,652,540 B1 | 11/2003 | Cole et al. | |
| 6,165,185 A | 12/2000 | Shennib et al. | 6,652,541 B1 | 11/2003 | Vargas et al. | |
| 6,171,320 B1 | 1/2001 | Monassevitch | 6,660,015 B1 | 12/2003 | Berg et al. | |
| 6,171,321 B1 | 1/2001 | Gifford, III et al. | 6,682,540 B1 | 1/2004 | Sancoff et al. | |
| 6,176,413 B1 | 1/2001 | Heck et al. | 6,695,859 B1 | 2/2004 | Golden et al. | |
| 6,176,864 B1 | 1/2001 | Chapman | 6,702,826 B2 | 3/2004 | Liddicoat et al. | |
| 6,179,840 B1 | 1/2001 | Bowman | 6,704,401 B2 | 3/2004 | Piepho et al. | |
| 6,179,848 B1 | 1/2001 | Solem | 6,709,442 B2 | 3/2004 | Miller et al. | |
| 6,179,849 B1 | 1/2001 | Yencho et al. | 6,712,829 B2 | 3/2004 | Schulze | |
| 6,183,512 B1 | 2/2001 | Howanec, Jr. et al. | 6,719,768 B1 | 4/2004 | Cole et al. | |
| 6,190,373 B1 | 2/2001 | Palermo et al. | 6,743,243 B1 | 6/2004 | Roy et al. | |
| 6,193,733 B1 | 2/2001 | Adams | 6,749,622 B2 | 6/2004 | McGuckin, Jr. et al. | |
| 6,193,734 B1 | 2/2001 | Bolduc et al. | 6,776,782 B2 | 8/2004 | Schulze | |
| 6,197,037 B1 | 3/2001 | Hair | 6,776,784 B2 * | 8/2004 | Ginn ........................... 606/151 | |
| 6,217,611 B1 | 4/2001 | Klostermeyer | 6,776,785 B1 | 8/2004 | Yencho et al. | |
| 6,221,083 B1 | 4/2001 | Mayer | 6,802,847 B1 | 10/2004 | Carson et al. | |
| 6,241,738 B1 | 6/2001 | Dereume | 6,821,286 B1 | 11/2004 | Carranza et al. | |
| 6,241,741 B1 | 6/2001 | Duhaylongsod et al. | 6,869,444 B2 | 3/2005 | Gabbay | |
| 6,248,117 B1 | 6/2001 | Blatter | 6,913,607 B2 | 7/2005 | Ainsworth et al. | |
| 6,250,308 B1 | 6/2001 | Cox | 6,918,917 B1 | 7/2005 | Nguyen et al. | |
| 6,254,615 B1 | 7/2001 | Bolduc et al. | 6,921,407 B2 | 7/2005 | Nguyen et al. | |
| 6,269,819 B1 | 8/2001 | Oz et al. | 6,926,730 B1 | 8/2005 | Nguyen et al. | |

| | | | | | | |
|---|---|---|---|---|---|---|
| 6,945,980 B2 | 9/2005 | Nguyen et al. | EP | 0140557 A2 | 5/1985 | |
| 6,955,679 B1 | 10/2005 | Hendricksen et al. | EP | 0326426 B1 | 8/1989 | |
| 6,960,221 B2 | 11/2005 | Ho et al. | EP | 0409569 B1 | 1/1991 | |
| 6,979,337 B2 | 12/2005 | Kato | EP | 0419597 B1 | 4/1991 | |
| 6,979,338 B1 | 12/2005 | Loshakove et al. | EP | 0432692 A1 | 6/1991 | |
| 7,022,131 B1 | 4/2006 | Derowe et al. | EP | 0478949 A1 | 4/1992 | |
| 7,056,330 B2 | 6/2006 | Gayton | EP | 0494636 B1 | 7/1992 | |
| 7,063,711 B1 | 6/2006 | Loshakove et al. | EP | 0537955 A2 | 4/1993 | |
| 7,070,618 B2 | 7/2006 | Streeter | EP | 0559429 B1 | 9/1993 | |
| 7,182,769 B2 | 2/2007 | Ainsworth et al. | EP | 0598529 A2 | 5/1994 | |
| 7,186,251 B2 * | 3/2007 | Malecki et al. .................. 606/41 | EP | 0632999 A1 | 1/1995 | |
| 7,220,268 B2 | 5/2007 | Blatter | EP | 0641546 A1 | 3/1995 | |
| 2001/0018592 A1 | 8/2001 | Schaller et al. | EP | 0656191 A2 | 6/1995 | |
| 2001/0018593 A1 | 8/2001 | Nguyen et al. | EP | 0687446 A2 | 12/1995 | |
| 2001/0018611 A1 | 8/2001 | Solem et al. | EP | 0705568 B1 | 4/1996 | |
| 2001/0021856 A1 | 9/2001 | Bolduc et al. | EP | 0705569 B1 | 4/1996 | |
| 2001/0047181 A1 | 11/2001 | Ho et al. | EP | 0711532 A1 | 5/1996 | |
| 2002/0010490 A1 | 1/2002 | Schaller et al. | EP | 0734697 B1 | 10/1996 | |
| 2002/0042623 A1 | 4/2002 | Blatter et al. | EP | 0778005 A1 | 12/1996 | |
| 2002/0082614 A1 | 6/2002 | Logan et al. | EP | 0815795 B1 | 1/1998 | |
| 2002/0099395 A1 | 7/2002 | Acampora et al. | GB | 2223410 A | 4/1990 | |
| 2002/0107531 A1 * | 8/2002 | Schreck et al. .................. 606/142 | JP | 07308322 | 11/1995 | |
| 2002/0151916 A1 | 10/2002 | Muramatsu et al. | JP | 08336544 | 12/1996 | |
| 2002/0165561 A1 | 11/2002 | Ainsworth et al. | JP | 10337291 | 12/1998 | |
| 2002/0173803 A1 | 11/2002 | Ainsworth et al. | RU | 2110222 C1 | 5/1998 | |
| 2003/0074012 A1 | 4/2003 | Nguyen et al. | SU | 577022 A1 | 10/1977 | |
| 2003/0078603 A1 | 4/2003 | Schaller et al. | SU | 1186199 A1 | 2/1983 | |
| 2003/0083742 A1 | 5/2003 | Spence et al. | SU | 1456109 A1 | 2/1989 | |
| 2003/0093118 A1 | 5/2003 | Ho et al. | SU | 1560133 A1 | 4/1990 | |
| 2003/0125755 A1 | 7/2003 | Schaller et al. | WO | 9006725 A1 | 6/1990 | |
| 2003/0191481 A1 | 10/2003 | Nguyen et al. | WO | 9009149 A1 | 8/1990 | |
| 2003/0195531 A1 | 10/2003 | Gardiner et al. | WO | 9014795 A2 | 12/1990 | |
| 2003/0199974 A1 | 10/2003 | Lee et al. | WO | 9107916 A1 | 6/1991 | |
| 2003/0225420 A1 * | 12/2003 | Wardle .................. 606/151 | WO | 9108708 A1 | 6/1991 | |
| 2004/0050393 A1 | 3/2004 | Golden et al. | WO | 9117712 A1 | 11/1991 | |
| 2004/0068276 A1 | 4/2004 | Golden et al. | WO | 9205828 A1 | 4/1992 | |
| 2004/0102797 A1 | 5/2004 | Golden et al. | WO | 9212676 A2 | 8/1992 | |
| 2004/0111099 A1 | 6/2004 | Nguyen et al. | WO | 9222041 A2 | 12/1992 | |
| 2004/0138685 A1 | 7/2004 | Clague et al. | WO | 9301750 A1 | 2/1993 | |
| 2004/0176663 A1 | 9/2004 | Edoga et al. | WO | 9415535 A1 | 7/1994 | |
| 2004/0193259 A1 | 9/2004 | Gabbay | WO | 9415537 A1 | 7/1994 | |
| 2005/0004582 A1 | 1/2005 | Edoga et al. | WO | 9600035 A1 | 1/1996 | |
| 2005/0021054 A1 | 1/2005 | Ainsworth et al. | WO | 9606565 A1 | 3/1996 | |
| 2005/0043749 A1 | 2/2005 | Breton et al. | WO | 9638090 A1 | 12/1996 | |
| 2005/0065601 A1 | 3/2005 | Lee et al. | WO | 9712555 A2 | 4/1997 | |
| 2005/0070924 A1 | 3/2005 | Schaller et al. | WO | 9716122 A1 | 5/1997 | |
| 2005/0075659 A1 | 4/2005 | Realyvasquez et al. | WO | 9727898 A1 | 8/1997 | |
| 2005/0075667 A1 | 4/2005 | Schaller et al. | WO | 9728744 A1 | 8/1997 | |
| 2005/0080454 A1 | 4/2005 | Drews et al. | WO | 9731575 A1 | 9/1997 | |
| 2005/0101975 A1 | 5/2005 | Nguyen et al. | WO | 9732526 A1 | 9/1997 | |
| 2005/0107871 A1 | 5/2005 | Realyvasquez et al. | WO | 9740754 A1 | 11/1997 | |
| 2005/0119675 A1 * | 6/2005 | Adams et al. .................. 606/151 | WO | 9742881 A1 | 11/1997 | |
| 2005/0131429 A1 | 6/2005 | Ho et al. | WO | 9819636 A2 | 5/1998 | |
| 2005/0177180 A1 * | 8/2005 | Kaganov et al. .................. 606/151 | WO | 9830153 A1 | 7/1998 | |
| 2005/0267572 A1 | 12/2005 | Schoon et al. | WO | 9842262 A1 | 10/1998 | |
| 2006/0004389 A1 | 1/2006 | Nguyen et al. | WO | 9848707 A1 | 11/1998 | |
| 2006/0052821 A1 * | 3/2006 | Abbott et al. .................. 606/213 | WO | 9852475 A1 | 11/1998 | |
| 2006/0253143 A1 | 11/2006 | Edoga et al. | WO | 9907294 A1 | 2/1999 | |
| 2006/0271081 A1 | 11/2006 | Realyvasquez | WO | 9912484 A1 | 3/1999 | |
| 2006/0293701 A1 | 12/2006 | Ainsworth et al. | WO | 9915088 A1 | 4/1999 | |
| 2007/0010835 A1 | 1/2007 | Breton et al. | WO | 9937218 A1 | 7/1999 | |
| 2007/0027461 A1 | 2/2007 | Gardiner et al. | WO | 9962406 | 12/1999 | |
| 2007/0106313 A1 | 5/2007 | Golden et al. | WO | 9962408 A1 | 12/1999 | |
| 2007/0142848 A1 | 6/2007 | Ainsworth et al. | WO | 9962409 | 12/1999 | |
| | | | WO | 9962415 A1 | 12/1999 | |
| | FOREIGN PATENT DOCUMENTS | | WO | 9963910 A1 | 12/1999 | |
| DE | 2703529 A1 | 8/1978 | WO | 9965409 A1 | 12/1999 | |
| DE | 3203410 A1 | 11/1982 | WO | 0003759 A2 | 1/2000 | |
| DE | 3227984 A1 | 2/1984 | WO | 0015144 A1 | 3/2000 | |
| DE | 3504202 A1 | 8/1985 | WO | 0059380 A2 | 10/2000 | |
| DE | 4133800 C1 | 1/1993 | WO | 0060995 A2 | 10/2000 | |
| DE | 4402058 C1 | 4/1995 | WO | 0064381 A1 | 11/2000 | |
| DE | 19547617 C1 | 9/1997 | WO | 0074603 A1 | 12/2000 | |
| DE | 19732234 A1 | 1/1999 | WO | 0119292 A1 | 3/2001 | |
| EP | 0072232 B1 | 2/1983 | WO | 0126557 A1 | 4/2001 | |
| EP | 0121362 B1 | 10/1984 | WO | 0126586 A1 | 4/2001 | |
| EP | 0122046 A1 | 10/1984 | WO | 0128432 A1 | 4/2001 | |
| EP | 0129441 B1 | 12/1984 | WO | 0154618 A | 8/2001 | |
| EP | 0130037 A1 | 1/1985 | WO | 0174254 A1 | 10/2001 | |

| | | | | | | | |
|---|---|---|---|---|---|---|---|
| WO | 0213701 | A1 | 2/2002 | WO | 02087425 | A2 | 11/2002 |
| WO | 0213702 | A1 | 2/2002 | WO | 03053289 | A1 | 7/2003 |
| WO | 0230295 | A1 | 4/2002 | WO | 03088875 | A1 | 10/2003 |
| WO | 0230298 | A1 | 4/2002 | WO | 2005011468 | A2 | 2/2005 |
| WO | 0234143 | A1 | 5/2002 | WO | 2005058170 | A1 | 6/2005 |
| WO | 02080779 | A1 | 10/2002 | | | | |
| WO | 02080780 | A1 | 10/2002 | | | | |

* cited by examiner

MEDICAL CLIP WITH RADIAL TINES, SYSTEM AND METHOD OF USING SAME

FIELD

The present invention relates generally to devices, systems and methods of drawing patient tissue together, and in particular such devices, systems and methods of drawing patient tissue together using a medical clip.

BACKGROUND

In many circumstances and for many reasons, it is often beneficial to capture and draw together two or more pieces of tissue of a patient. The location of the tissue and the circumstances of the need to draw the pieces of tissue together have long resulted in a variety of different devices and methods for drawing the tissue together. Devices such as bandages, both self-adhesive and otherwise, clamps and stitches have been used to capture pieces of tissue and draw them together. Once tissue is drawn together, the natural healing abilities of the body may then allow the pieces of tissue to grow together, over time sealing a gap between the pieces of tissue such that the device is no longer needed. Alternatively, the pieces of tissue may be held together by the device indefinitely, or for a particular period of time.

But, dependent on the location of the tissue, certain devices and methods may be impractical to utilize. For instance, while stitches may lend themselves well to readily accessible patient tissue, such as skin and muscle tissue, relatively inaccessible tissue, such as that found in the organs of the patient, may be impractical to capture and draw together using stitches. As such, the use of stitches to treat a defect in a patient's heart may tend require a traumatic open heart procedure, and even then, because the interior of the heart still may not be readily accessible, the treatment of a defect inside the heart may still not be attainable with stitches. Thus, a common device and method for drawing together patient tissue may not be applicable for all situations, particularly those involving a defect in organs of the patient such as the heart.

One relatively common defect in the heart of newborn children, which may also be present in older children and in adults, is a patent foramen ovale ("PFO"). During the gestation of a fetus in the womb, blood is oxygenated not by the undeveloped lungs of the fetus, but rather by the placenta of the mother. However, the heart of the fetus nevertheless pumps the blood through the cardiovascular system and receives the blood from the cardiovascular system. As such, in order to avoid the undeveloped lungs of the fetus, various vessels and bypasses exist that operate only during gestation that divert the blood from the lungs. At birth these bypasses typically close and circulation occurs by way of the lungs as with a normally developed adult.

An opening between the right atrium and the left atrium called the foramen ovale is open during gestation to prevent transfer of blood from the right ventricle of the heart to the lungs during gestation. Upon birth, the child's inherent circulation creates pressure within the atrium which causes a flap of tissue to close over the foramen ovale. As the child matures, the flap of tissue develops into a permanent closure. However, in some children the flap of tissue does not close, either in whole or in part, over the entire foramen ovale, creating a patent foramen ovale. The continued existence of the foramen ovale results in continued diversion from the lungs of at least some of the child's blood, reducing the flow of oxygenated blood through the child's system, and potentially leading to serious complications to the health of the child.

It is recognized that although PFO may occur most prominently in children and, in particular, relatively newborn children, that the PFO may also occur or be present in older children and in adults.

Other cardiac defects are known to exist beyond patent foramen ovales. For instance, atrial-septal defects ("ASD") and ventricular-septal defects ("VSD") likewise sometimes occur and may be detrimental to the health of the person, e.g., a child. Historically, open heart surgery had been required to fix such defects. But open heart surgery carries with it serious and well-known and recognized risks to the well-being of the person, in addition to being expensive and a considerable burden on hospital resources.

Closure devices for treating heart defects, such as patent foramen ovales, have been developed.

U.S. Pat. No. 6,776,784, Ginn, Clip Apparatus For Closing Septal Defects and Methods of Use, (Core Medical, Inc.) discloses a device for closing a septal defect, such as a patent foramen ovale, includes a clip formed from a superelastic material that is inserted into a septum wall of a heart. The clip is advanced through a patient's vasculature, e.g., within a delivery apparatus, until the clip is disposed within a first chamber adjacent the septal defect. Tines of the clip are directed through a flap of tissue of the septal defect until the tines of the clip are disposed within a second opposing chamber. The clip then transforms into its relaxed state, wherein the tines of the clip engage with a surface of the second chamber, thereby substantially closing the septal opening.

U.S. Patent Application Publication No. US2007/0060858, Sogard et al, Defect Occlusion Apparatus, System and Method, discloses occluding a multiplicity of parallel membranes, such as found in a patent foramen ovale. The methods, apparatus, and systems include the use of a positioning device that can be seated on the limbus of the septum secundum. The positioning device includes a piercing member that can pierce the septum secundum and septum primum. The positioning device also includes a fastening member that can engage the septum secundum and septum primum to fasten the tissues and thereby occlude a patent foramen ovale.

U.S. Pat. No. 7,220,265, Chanduszko et al, Patent Foramen Ovale (PFO) Closure Method and Device, (NMT Medical, Inc.) discloses methods and devices for closing two overlapping layers of tissue in a mammalian heart, such as a patent foramen ovale. The closure devices may take a number of different forms and may be retrievable. In some embodiments, the closure devices may be delivered with a catheter capable of puncturing mammalian tissue. In some embodiments, a spring-like bioabsorbable polymer material are used, in one such embodiment as a "grappling hook", to embed in and draw together the pieces of tissue. In another embodiment, a suture is delivered, and an anchor forms a pre-determined shape and engages the septum secundum, closing the patent foramen ovale.

SUMMARY

Closure devices for treating patent foramen ovales have been developed that allow for the treatment of patent foramen ovales and other cardiac defects without conducting open heart surgery. Instead, the closure devices may be utilized to cure or treat cardiac defects by way of transveneous implantation. With the device placed in a sheath attached to a catheter small enough to pass through the blood vessels of the child and into the heart, the device may be deployed in the heart to treat the cardiac defect.

The device itself may be made of a number of joined tines, each of which form a loop, perhaps sharpened at the end to allow for puncturing the cardiac tissue of the patient. Outside of the implantation sheath each tine may be biased so that each tine forms a loop or coil in a relaxed state. Inside of the sheath the tines are uncoiled to be relative linear, possibly giving the device an adequately small profile to allow passage of the device through a vein or other vascular component of the patient. When the device is deployed from the sheath the tines may curl into a biased (relaxed) coiled form. During a transition from a relatively linear configuration to a coiled configuration, as the device is deployed from the sheath, within the heart the sharpened end of the tines may pass through cardiac tissue. In the case of the treatment of a patent foramen ovale, if the device is positioned adjoining the two flaps of tissue which did not automatically close together, at least one approximately linear tine may pass through each flap of tissue as coils are formed. As the tines complete forming a coil, the two flaps of tissue may be drawn together, either closing the foramen ovale altogether, or bringing the flaps of tissue in closer proximity of each other such that vascular pressure may ultimately bring the flaps of tissue together. As the patient matures flaps of tissue may grow together and the foramen ovale close permanently.

In an embodiment, a medical clip is disclosed for drawing together patient tissue. The medical clip comprises a central hub having an axis and a plurality of tines coupled to the central hub. Each individual one of the plurality of tines has a tip and is resiliently biased to form a coil with the tip pointing radially outward from the axis with an approximately common angle between adjacent ones of the plurality of tines.

In an embodiment, each of the plurality of tines may be flexed to be approximately linear.

In an embodiment, each coil of each individual one of the plurality of tines comprises at least one full revolution.

In an embodiment, each coil of each individual one of the plurality of tines comprises at least one-and-a-quarter revolutions.

In an embodiment, the plurality of tines are configured to pass through the patient tissue.

In an embodiment, the plurality of tines are configured to draw a first piece of the patient tissue together with a second piece of the patient tissue.

In an embodiment, at least one of the plurality of tines passes through the first piece of the patient tissue and at least one other one of the plurality of tines passes through the second piece of the patient tissue during a transition from being approximately linear to being coiled.

In an embodiment, the first piece of the patient tissue is drawn together with the second piece of the patient tissue when the plurality of tines are coiled.

In an embodiment, the tips point approximately orthogonal to the axis.

In an embodiment, the plurality of tines are comprised of nitinol.

In an embodiment, a system for drawing together patient tissue is disclosed. The system comprises a medical clip, comprising a central hub having an axis and a plurality of tines coupled to the central hub. Each individual one of the plurality of tines has a tip and is resiliently biased to form a coil with the tip pointing radially outward from the axis with an approximately common angle between adjacent ones of the plurality of tines. The system further comprises a delivery catheter. The delivery catheter comprises a lumen containing the medical clip with each of the plurality of tines being flexed to be approximately linear by the delivery catheter and a deployment mechanism positioned within the lumen adapted to deploy the medical clip by pushing the medical clip out of an opening in the delivery catheter. Each of the plurality of tines form into the coil when the medical clip is deployed from the delivery catheter.

In an embodiment, a medical clip is disclosed for drawing together patient tissue. The medical clip comprises a central hub having an axis and four tines coupled to the central hub. Each individual one of the four tines has a tip and is resiliently biased to form a coil with the tip pointing radially outward from the axis with an approximately common angle between adjacent ones of the four tines.

In an embodiment, each of the four tines may be flexed to be approximately linear.

In an embodiment, each coil of each individual one of the four tines comprises at least one full revolution.

In an embodiment, each coil of each individual one of the four tines comprises at least one-and-a-quarter revolutions.

In an embodiment, the four tines are configured to pass through the patient tissue.

In an embodiment, the four tines are configured to draw a first piece of the patient tissue together with a second piece of the patient tissue.

In an embodiment, at least one of the four tines passes through the first piece of the patient tissue and at least one other one of the four tines passes through the second piece of the patient tissue during a transition from being approximately linear to being coiled.

In an embodiment, the first piece of the patient tissue is drawn together with the second piece of the patient tissue when the four tines are coiled.

In an embodiment, the tips point approximately orthogonal to the axis.

In an embodiment, the four tines are comprised of nitinol.

In an embodiment, a method is disclosed for drawing together tissue of a patient using a medical clip having a central hub coupled to a plurality of tines each resiliently biased to form a coil with a tip pointing radially outward from an axis of the central hub with an approximately common angle between adjacent ones of the plurality of tines. The method comprises the steps of placing a delivery catheter having a lumen containing the medical clip between a first piece of the tissue and a second piece of the tissue, wherein the plurality of tines are straightened while in the delivery catheter and deploying the medical clip from the delivery catheter. At least one of the plurality of tines passes through the first piece of tissue and at least one other of the plurality of tines passes through the second piece of tissue. The first piece of tissue and the second piece of tissue are drawn together when the plurality of tines coil.

In an embodiment, a method is disclosed for treating a patent foramen ovale using a medical clip having a central hub coupled to a plurality of tines each resiliently biased to form a coil with a tip pointing radially outward from an axis of the central hub with an approximately common angle between adjacent ones of the plurality of tines. The method comprises the steps of placing a delivery catheter having a lumen containing the medical clip between a first piece of tissue of the patent foramen ovale and a second piece of tissue of the patent foramen ovale, wherein the plurality of tines are straightened while in the delivery catheter and deploying the medical clip from the delivery catheter. At least one of the plurality of tines passes through the first piece of tissue of the patent foramen ovale and at least one other of the plurality of tines passes through the second piece of tissue of the patent foramen ovale. The patent foramen ovale is reduced in size when the first piece of tissue of the patent foramen ovale and the second piece of tissue of the patent foramen ovale are drawn together when each of the plurality of tines form the coil.

In an embodiment, the patent foramen ovale is substantially closed when each of the plurality of tines form the coil.

DRAWINGS

DESCRIPTION

It is often advantageous to capture and draw together pieces of tissue of a patient. Doing so may close and help wounds heal, or close defects in patient organs. Various capture and closure devices exist, but while such devices may be effective in certain situations and under certain conditions, they may be ineffective or disadvantageous in other conditions. Particularly in situations where the tissue to be drawn together is not readily accessible to personal manipulation, commonly known devices are often of limited use. The treatment of cardiac defects may be one such relatively common situation.

In order to treat cardiac defects such as a patent foramen ovale, it is desirable close the gap between flaps of cardiac tissue without having to experience the trauma and expense of open heart surgery. Accordingly, a medical clip and delivery system has been developed that may be inserted into the heart intravenously. Upon positioning the delivery system within the gap of the patent foramen ovale, a deployment system deploys the medical clip. The physical nature of the medical clip captures and draws together the flaps of tissue of the patent foramen ovale, thereby reducing or closing the gap altogether.

Figure 1:
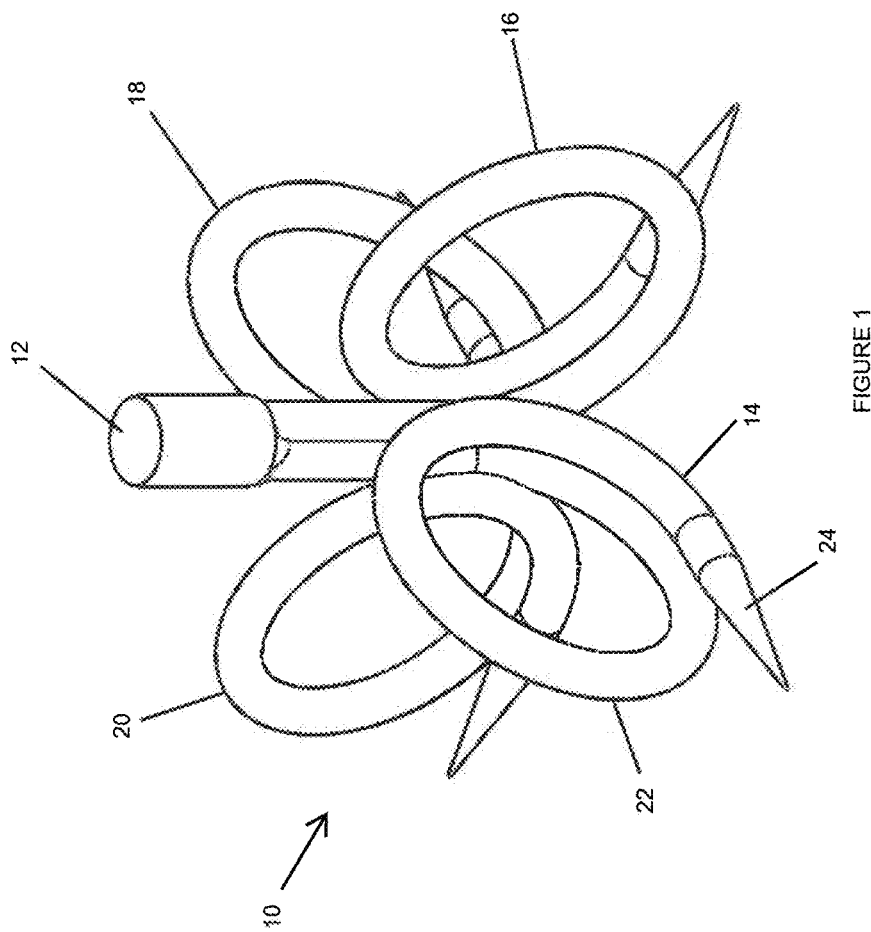
FIG. 1 shows a medical clip for drawing together patient tissue.

An embodiment of a medical clip for treating cardiac defects is illustrated in FIG. 1. Clip 10 has central hub 12. Four tines 14, 16, 18, 20 project from central hub 12. In alternative embodiments more or fewer tines 14, 16, 18, 20 than four are utilized. Each tine 14, 16, 18, 20 is comprised of coil 22 and end 24. In an embodiment, end 24 forms a sharpened tip. In the illustrated embodiment, tines 14, 16, 18, 20 are coupled to central hub 18, with end 24 of each tine 14, 16, 18, 20 pointing radially outward from central hub 12.

Tines 14, 16, 18, 20 may be made from a variety of different materials. Any material may be used such that tines 14, 16, 18, 20 may be resiliently biased to form coil 22 when clip 10 has been deployed, provided the material is biocompatible or may be treated to make it biocompatible. In an embodiment, tines 14, 16, 18, 20 are made from the shaped memory alloy Nitinol. In alternative embodiments, biocompatible elastic material such as stainless steel may be utilized. Biocompatible super-elastic materials may also be utilized. Super-elastic materials could encompass super-elastic plastics and super-elastic metals. A super-elastic plastic generally is any material that has shape memory ability after shaped setting, e.g.,
materials described in the Massachusetts Institute of Technology, News Office article entitled "Intelligent Plastics Change Shape With Light, dated Apr. 13, 2005, authored by Elizabeth A. Thomson, which is hereby incorporated by references in its entirety. Super-elastic metals are sometimes known as a shape memory alloy (also, smart metal, memory alloy or muscle wire) that remembers its shape and can be returned to that shape after being deformed, by applying heat to the alloy. When the shape memory effect is correctly harnessed, super-elastic metals becomes a lightweight, solid-state alternative to conventional actuators such as hydraulic, pneumatic and motor-based systems. In an embodiment, drawn filled tubes filled with a super-elastic material or materials.

In a further alternative embodiment, spring-like bioabsorbable material may be utilized, which may result in clip 10 ultimately dissolving. Alternatively, a non-bioabsorbable material may be utilized to form clip 10, but the material may be coated with biological tissue, bioabsorbable polymer, a therapeutic substance or other substance which may be advantageously delivered to the treatment site concurrent with clip 10.

In the illustrated embodiment of FIG. 1, coils 22 create a full circular loop, whereby a completed circle is formed because individual tines 14, 16, 18, 20 complete an approximately circular circuit. As illustrated, tines 14, 16, 18, 20 complete one-and-a-quarter revolutions, with the overlap providing potentially enhanced ability to hold tissue over a coil which completes only one full revolution. Alternatively, coils 22 may form only a partial circular loop. In an embodiment, coil 22 may be only three-quarters of a completed circle. In such an embodiment, the tissue captured in coil 22 may be sufficiently secured that the flaps of tissue may be drawn together even without coil 22 forming a completed circle. Alternative partial loops may also be utilized such that the tissue may still be captured and retained by coil 22. In further alternative embodiments, non-circular loops may also be utilized. Oval or ellipsoid shapes may be utilized advantageously in certain circumstances. Alternatively, shapes with angles such as triangles or rectangles may be utilized. Further, irregular shapes may be utilized.

Figure 2:
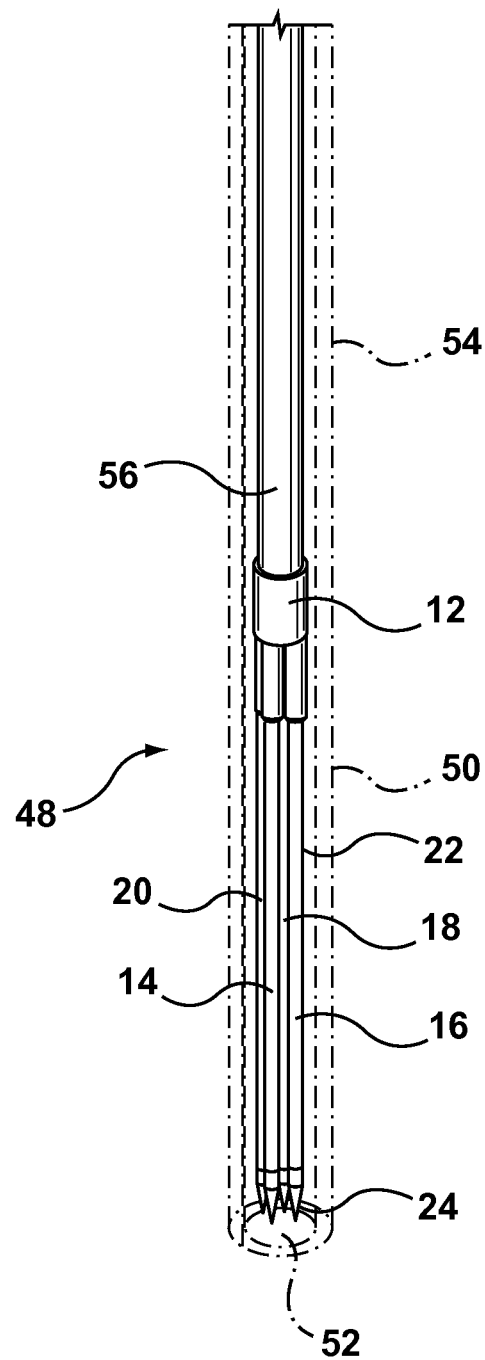
FIG. 2 shows the medical clip of FIG. 1 positioned in a deployment catheter.

FIG. 2 illustrates an embodiment of clip 10 in an embodiment of a deployment catheter 48 having sheath 50. To place clip 10 in sheath 50, central hub 12 may be drawn into lumen 52 of sheath 50. As central hub 12 is drawn in to sheath 50, coil 22 of each tine 14, 16, 18, 20 is stressed by sheath 50, causing coil 22 to unwind and each tine 14, 16, 18, to become approximately straight when positioned in sheath 50. End 24 of each tine 14, 16, 18, 20 remains in proximity of the distal end of sheath 50.

Sheath 50 may be coupled to catheter 54 to form deployment catheter 48. Catheter 54 may be utilized to guide sheath 50 into position to deploy clip 10. Catheter 54 may also be utilized to deploy clip 10. In an embodiment, catheter 54 has a deployment mechanism 56 in contact with central hub 12. When deployment mechanism 56 pushes central hub 12, clip 10 slides along sheath 50 until clip 10 has fully emerged from sheath 50.

Figure 3:
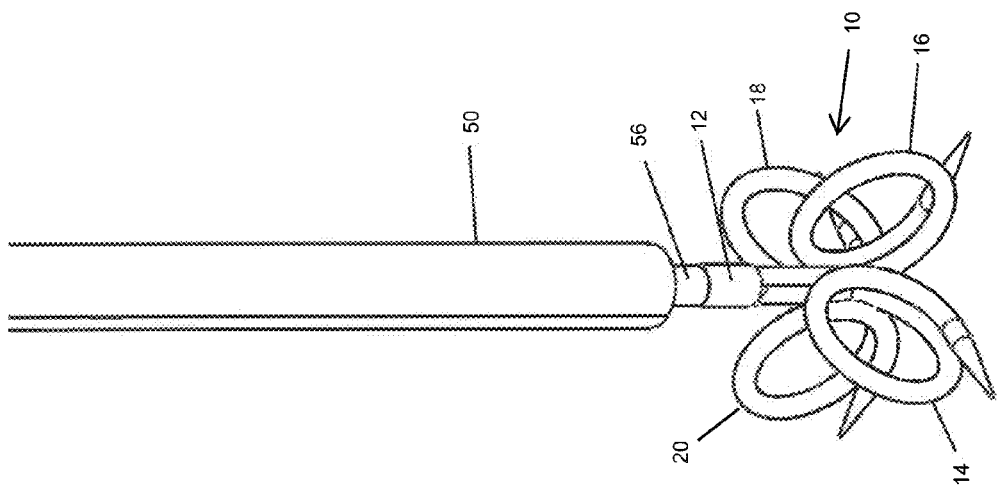
FIG. 3 shows the medical clip of FIG. 1 deployed from, but still coupled to the deployment catheter.

FIG. 3 illustrates an embodiment of clip 10 fully emerged from sheath 50 but still attached to deployment mechanism 56. In the illustrated embodiment, tines 14, 16, 18, 20 have returned to their resiliently biased coiled state. In various embodiments of clip 10, dependent on the material from which tines 14, 16, 18, 20 were made, tines 14, 16, 18, 20 may coil within moments of emerging from sheath 50, or may require a lengthier amount of time to coil. In certain embodiments, tines 14, 16, 18, 20 may, for a time, remain essentially straight even after central hub 12 has emerged from sheath 50 due to the length of time required to coil. However, in such an embodiment, tines 14, 16, 18, 20 will eventually coil after clip 10 has deployed from sheath 50.

Figure 4A:
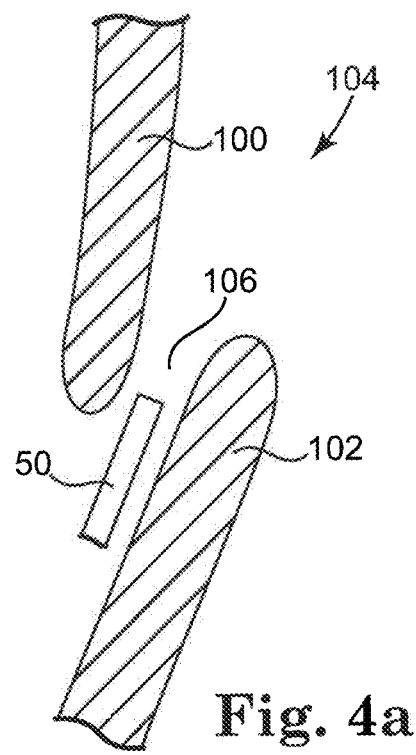
FIGS. 4a-4c illustrate the positioning and deployment of the medical clip of FIG. 1 for the treatment of a patent foramen ovale.
Figure 4B:
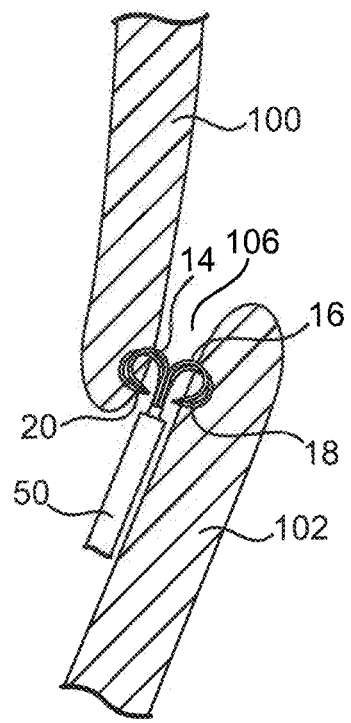
Figure 4C:
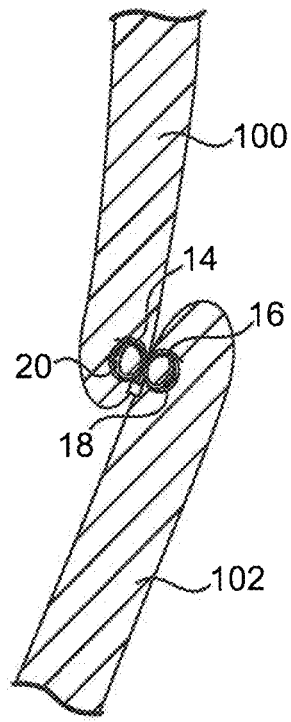
Figure 5:
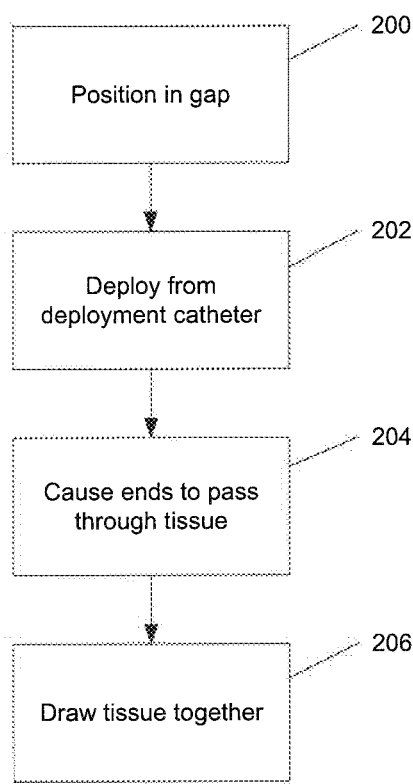
FIG. 5 is a flowchart for implanting a medical clip.

FIGS. 4a-4c and the flowchart of FIG. 5 illustrate a use of clip 10 and sheath 50 in the treatment of a patent foramen ovale. Sheath 50 is positioned (FIG. 5, 200) in a gap 106 between a first flap of tissue 100 and a second flap of tissue 102 within heart 104 while clip 10 remains in sheath 50 with tines 14, 16, 18, 20 uncoiled (FIG. 4a). As clip 10 is deployed (FIG. 5, 202) from sheath 50, tines 14, 16, 18, 20 begin to coil, with the coiling motion causing (FIG. 5, 204) end 24 of at least one tine 14, 16, 18, 20 passing through tissue 100 and end 24 of at least one other tine 14, 16, 18, 20 passing through tissue 102 (FIG. 4b). As tines 14, 16, 18, 20 complete coiling, tissue 100 and tissue 102 are drawn (FIG. 5, 206) together by the decrease in the radius of coil 22 as each tine 14, 16, 18, 20 coils. The completion of coiling may draw tissue 100 and tissue 102 completely together and close gap 106 (FIG. 4c). Alternatively, the completion of coiling may draw tissue 100 and tissue 102 nearly together though still leaving a reduced gap 106.

The treatment of other cardiac defects, such as atrial-septal defects ("ASD") and ventricular-septal defects ("VSD"), by the same steps illustrated above is also contemplated. In fact, any patient condition in which it is desirable to join or draw together two flaps of tissue may be effectively treated utilizing the steps illustrated in FIGS. 4a-4c. While the physical dimensions of clip 10 and delivery catheter 54 may need to change to reflect the different conditions, such as a wider gap 106 or tougher or thicker tissue 100, 102, the method of using clip 10 may remain unchanged.

In various implementations of the deployment of clip 10, tissue 100 and tissue 102 may be drawn together even if one or two of tines 14, 16, 18, 20 do not pass through tissue as intended. So long as at least one tine 14, 16, 18, 20 passes through each flap of tissue 100, 102, tissue 100 may be drawn together with tissue 102. Instances in which all four tines 14, 16, 18, 20 pass through tissue 100, 102 may, however, create the highest likelihood of maximizing the amount of tissue 100, 102 brought together.

The geometry of the components of clip 10 influence performance of clip 10. Relatively longer tines 14, 16, 18, 20 and relatively greater diameter of coil 22 may allow for the treatment of a relatively larger gap 106, or result in greater depth of penetration of tissue 100, 102, perhaps increasing the likelihood of closing gap 106 altogether. And a relatively greater diameter of the material comprising tines 14, 16, 18, 20 may increase the ability of tines 14, 16, 18, 20 to hold tissue 100, 102 and decrease the likelihood of tissue 100, 102 slipping out of tines 14, 16, 18, 20 during or after coiling. In an embodiment, the dimensions of coil 22 is approximately 0.090 inches, and the diameter of tines 14, 16, 18, 20 is 0.014 inches.

Figure 6:
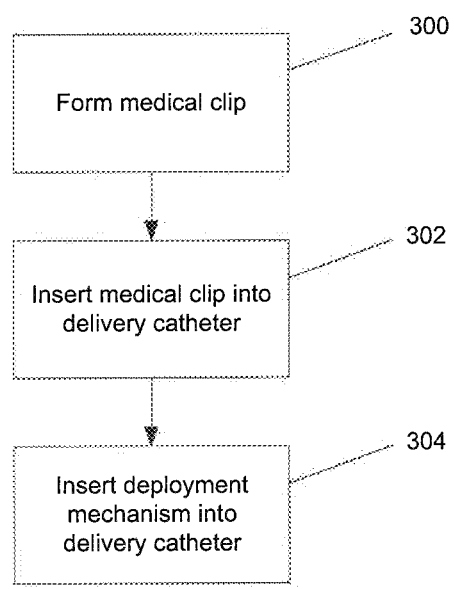
FIG. 6 is a flowchart for making a system including a medical clip positioned in a deployment catheter.

FIG. 6 is a flowchart of a method for making an system in which an embodiment of medical clip 10 is positioned in deployment catheter 48. Medical clip 10 is formed (300) by coupling tines 14, 16, 18, 20 to central hub 12. Medical clip 10 is inserted (302) into lumen 52 of delivery catheter 48. In an embodiment, central hub 12 is inserted into lumen 52 first, followed by tines 14, 16, 18, 20. As the insertion occurs, tines 14, 16, 18, uncoil until they are approximately linear within lumen 52. Deployment mechanism 56 is inserted (304) into lumen 52, such that when the deployment mechanism is used, medical clip 10 deploys out of lumen 52 and tines 14, 16, 18, 20 coil. In embodiments where deployment mechanism 56 is coupled to medical clip 10, coupling deployment mechanism 56 to medical clip 10 may occur either before or after insertion of medical clip into delivery catheter 48. When coupling occurs before insertion of medical clip 10, deployment mechanism 56 may be utilized to insert medical clip 10 into deployment catheter 48 by pulling medical clip into lumen 52.

Thus, embodiments of the devices, system and methods of drawing patient tissue together are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for drawing together patient tissue, comprising:
   a medical clip including:
   a central hub having a hub axis; and
   a plurality of tines each having a tine axis, said plurality of tines coupled to said central hub;
   wherein each individual one of said plurality of tines has a sharpened tip and is resiliently biased to form a coil with said tip pointing radially outward from said hub axis with an approximately common angle between adjacent ones of said plurality of tines;
   wherein each coil of each individual one of said plurality of tines comprises at least one full revolution winding about a central axis orthogonal to said hub axis; and
   a sheath comprising a lumen, said clip being configured to be drawn into said lumen;
   wherein each of said plurality of tines may be flexed to be approximately linear when said clip is drawn into said sheath; and
   wherein each tine axis of each of said plurality of tines is parallel to said hub axis when said clip is drawn into said sheath.

2. The system of claim 1 wherein each coil of each individual one of said plurality of tines comprises at least one-and-a-quarter revolutions.

3. The system of claim 1 wherein said plurality of tines are configured to pass through said patient tissue.

4. The system of claim 1 wherein said plurality of tines are configured to draw a first piece of said patient tissue together with a second piece of said patient tissue.

5. The system of claim 4 wherein at least one of said plurality of tines is adapted to pass through said first piece of said patient tissue and at least one other one of said plurality of tines is adapted to pass through said second piece of said patient tissue during a transition from being approximately linear to being coiled.

6. The system of claim 5 wherein said first piece of said patient tissue is drawn together with said second piece of said patient tissue when said plurality of tines are coiled.

7. The system of claim 1 wherein said tips point approximately orthogonal to said hub axis.

8. The system of claim 1 wherein said plurality of tines are comprised of nitinol.

9. A system for drawing together patient tissue, comprising:
   a medical clip, comprising:
   a central hub having a hub axis; and
   a plurality of tines each having a tine axis, said plurality of tines coupled to said central hub;
   wherein each individual one of said plurality of tines has a sharpened tip and is resiliently biased to form a coil with said tip pointing radially outward from said hub axis with an approximately common angle between adjacent ones of said plurality of tines; and a delivery catheter, comprising:
a lumen containing said medical clip with each of said plurality of tines being flexed to be approximately linear by said delivery catheter;
wherein each tine axis of each of said plurality of tines is parallel to said hub axis when said clip is contained in said lumen; and
a deployment mechanism positioned within said lumen adapted to deploy said medical clip by pushing said medical clip out of an opening in said delivery catheter;
wherein each of said plurality of tines form into said coil when said medical clip is deployed from said delivery catheter; and
wherein each coil of each individual one of said plurality of tines comprises at least one full revolution winding about a central axis orthogonal to said hub axis.

10. The system of claim 9 wherein each coil of each individual one of said plurality of tines comprises at least one-and-a-quarter revolutions.

11. The system of claim 9 wherein said plurality of tines are configured to pass through said patient tissue.

12. The system of claim 9 wherein said plurality of tines are configured to draw a first piece of said patient tissue together with a second piece of said patient tissue.

13. The system of claim 12 wherein at least one of said plurality of tines is adapted to pass through said first piece of said patient tissue and at least one other one of said plurality of tines is adapted to pass through said second piece of said patient tissue during a transition from being approximately linear to forming said coil.

14. The system of claim 13 wherein said first piece of said patient tissue is drawn together with said second piece of said patient tissue when said plurality of tines form said coil.

15. The system of claim 9 wherein said tips point approximately orthogonal to said hub axis.

16. The system of claim 9 wherein said plurality of tines are comprised of nitinol.

17. A method for drawing together tissue of a patient using a medical clip having a central hub having a hub axis coupled to a plurality of tines each having a tine axis, each of said tines resiliently biased to form a coil with a tip pointing radially outward from said hub axis of said central hub with an approximately common angle between adjacent ones of said plurality of tines, comprising the steps of:
placing a delivery catheter having a lumen containing said medical clip between a first piece of said tissue and a second piece of said tissue, wherein said plurality of tines are straightened such that each tine axis of each of said plurality of tines is parallel to said hub axis while in said delivery catheter;
deploying said medical clip from said delivery catheter;
wherein at least one of said plurality of tines passes through said first piece of tissue and at least one other of said plurality of tines passes through said second piece of tissue; and
wherein said first piece of tissue and said second piece of tissue are drawn together when said plurality of tines form said coil; and
wherein each coil of each individual one of said plurality of tines comprises at least one full revolution winding about a central axis orthogonal to said hub axis.

18. A method for treating a patent foramen ovale using a medical clip having a central hub having a hub axis coupled to a plurality of tines each having a tine axis, each of said tines resiliently biased to form a coil with a tip pointing radially outward from a hub axis of said central hub with an approximately common angle between adjacent ones of said plurality of tines, comprising the steps of:
placing a delivery catheter having a lumen containing said medical clip between a first piece of tissue of said patent foramen ovale and a second piece of tissue of said patent foramen ovale, wherein said plurality of tines are straightened such that each tine axis of each of said plurality of tines is parallel to said hub axis while in said delivery catheter;
deploying said medical clip from said delivery catheter;
wherein at least one of said plurality of tines passes through said first piece of tissue of said patent foramen ovale and at least one other of said plurality of tines passes through said second piece of tissue of said patent foramen ovale; and
wherein said patent foramen ovale is reduced in size when said first piece of tissue of said patent foramen ovale and said second piece of tissue of said patent foramen ovale are drawn together when each of said plurality of tines form said coil; and
wherein each coil of each individual one of said plurality of tines comprises at least one full revolution winding about a central axis orthogonal to said hub axis.

19. A method as in claim 18 wherein said patent foramen ovale is substantially closed when each of said plurality of tines forms said coil.

* * * * *